(12) United States Patent
Ho et al.

(10) Patent No.: US 11,723,946 B2
(45) Date of Patent: Aug. 15, 2023

(54) METHODS FOR REGULATING TRANSCRIPTION OF MULTIPLE GENES AND EXPRESSION OF MULTIPLE TARGETS

(71) Applicant: CHINA MEDICAL UNIVERSITY, Taichung (TW)

(72) Inventors: Tin-Yun Ho, Taichung (TW); Chien-Yun Hsiang, Taichung (TW)

(73) Assignee: CHINA MEDICAL UNIVERSITY, Taichung (TW)

( * ) Notice: Subject to any disclaimer, the term of this patent is extended or adjusted under 35 U.S.C. 154(b) by 233 days.

(21) Appl. No.: 17/212,951

(22) Filed: Mar. 25, 2021

(65) Prior Publication Data

US 2021/0236585 A1 Aug. 5, 2021

Related U.S. Application Data

(63) Continuation-in-part of application No. 15/898,989, filed on Feb. 19, 2018, now abandoned, which is a continuation of application No. 14/791,130, filed on Jul. 2, 2015, now abandoned.

(30) Foreign Application Priority Data

Aug. 25, 2014 (TW) .................................. 103129210

(51) Int. Cl.
*A61K 38/10* (2006.01)
*A61K 38/07* (2006.01)
*A61K 38/16* (2006.01)
*C07K 14/415* (2006.01)

(52) U.S. Cl.
CPC ............ *A61K 38/07* (2013.01); *A61K 38/168* (2013.01); *C07K 14/415* (2013.01)

(58) Field of Classification Search
CPC .. A61P 3/10; A61P 29/00; A61P 11/00; A61P 1/16; A61P 21/00; A61P 25/32; A61P 17/02; A61P 13/12; A61P 3/00; A61K 38/00; A61K 36/42; C07K 16/2863
See application file for complete search history.

(56) References Cited

U.S. PATENT DOCUMENTS 8,476,229 B2 7/2013 Ho et al.
2011/0124557 A1* 5/2011 Ho .......................... A61K 38/04
514/6.9

OTHER PUBLICATIONS

Ahmed N., "Glycation and diabetic complications," J Pak Med Assoc, Jul. 1991; 41(7):171 -4. PMID: 1920764 (7 pages).

* cited by examiner

*Primary Examiner* — Aradhana Sasan
*Assistant Examiner* — Jia-Hai Lee
(74) *Attorney, Agent, or Firm* — Muncy, Geissler, Olds & Lowe, P.C.

(57) ABSTRACT

Methods for regulating multiple organs, multiple genes and multiple targets by using a polypeptide. The polypeptide includes the amino acid sequence of SEQ ID No. 1 and/or homology thereof. The polypeptide reveals the potency to regulate transcription of multiple genes and expression of multiple targets. Therefore, a composition having the polypeptide can be applied to regulate the expression of multiple targets in multiple organs of patients. Furthermore, the composition having the polypeptide can be applied in therapies of inflammation and inflammatory disorders, suppression of fatty liver disease progression, suppression of the diseases caused by fatty accumulation, prevention and therapy of muscular atrophy, and avoiding the complications of diabetes.

6 Claims, 12 Drawing Sheets
(8 of 12 Drawing Sheet(s) Filed in Color)
Specification includes a Sequence Listing.

Group 1　　　　　　Group 2　　　　　　Group 3

Group 1　　　　　　Group 2　　　　　　Group 3 the control group    the experimental group the control group    the experimental group the control group    the experimental group the control group    the experimental group

SEQUENCE LISTING

```
<160> NUMBER OF SEQ ID NOS: 1

<210> SEQ ID NO 1
<211> LENGTH: 68
<212> TYPE: PRT
<213> ORGANISM: Artificial Sequence
<220> FEATURE:
<223> OTHER INFORMATION: Artificial synthsis

<400> SEQUENCE: 1

Ser Arg Cys Gln Gly Lys Ser Ser Trp Pro Gln Leu Val Gly Ser Thr
1               5                   10                  15

Gly Ala Ala Ala Lys Ala Trp Ile Glu Arg Glu Asn Pro Arg Val Arg
            20                  25                  30
```

```
Ala Val Ile Ile Lys Val Gly Ser Gly Ala Thr Lys Asp Phe Arg Cys
        35                  40                  45

Asp Arg Val Arg Val Trp Val Thr Glu Arg Gly Ile Val Ala Arg Pro
        50                  55                  60

Pro Thr Ile Gly
65
```

METHODS FOR REGULATING TRANSCRIPTION OF MULTIPLE GENES AND EXPRESSION OF MULTIPLE TARGETS

CROSS-REFERENCE TO RELATED APPLICATIONS

This application is a Continuation-in-Part of co-pending application Ser. No. 15/898,989, filed on Feb. 19, 2018, for which priority is claimed under 35 U.S.C. § 120; and this application claims priority of Application No. 103129210 filed in Taiwan on Aug. 25, 2014 under 35 U.S.C. § 119; the entire contents of all of which are hereby incorporated by reference.

BACKGROUND OF THE INVENTION

Field of the Invention

This invention discloses the second use of a polypeptide, specially, methods for regulating transcription of multiple genes and expression of multiple targets by using the polypeptide. The polypeptide comprising the amino acids sequence of SEQ ID No. 1 and/or its homology with replacement, deletion, insertion of one or multiple amino acids.

Brief Description of the Related Art

Upon advance of biomedical technology, many investigations have revealed the effects of various genes, growth factors, signaling transduction pathways and targets on occurrence and progression of diseases. Therefore, the drug development for target therapy is achievable upon the knowledge background of the relationship between targets and diseases. So far, most developed drugs for target therapy are applied to cancer therapy by directly suppressing the oncogene expression that is the leading cause of cancer progression. For example, the treatment of target therapy drugs including Iressa and Tarceva on lung cancer patients carrying epidermal growth factor receptor (EGFR) mutations brings the better therapeutic outcome and milder side effects than the traditional therapy.

Furthermore, Pemetrexed, developed by Eli Lilly and Company, is next generation of anticancer drug that targets metabolism through affecting on multiple targets. Pemetrexed is able to inhibit several critical enzymes of folate metabolism pathway that is required for DNA replication and cancer progression through affecting several critical enzymes in folate metabolism. Practically, the clinical trials had suggested that Pemetrexed reveals the significant suppression effect on cancer progression. Herein, treatments of Pemetrexed reveal therapeutic effect on multiple types of cancer. Recently, Pemetrexed was successively approved by the FDA for the therapies of pleural malignant mesothelioma and advanced stage of non-small cell lung cancer. Moreover, a large-scale multi-centers international phase III trial revealed that treatment of Pemetrexed in combination with Cisplatin improved the efficacy and prolonged the life span on patients with pleural malignant mesothelioma that is untreatable by surgical procedure. In addition, another large-scale phase III trial indicated that treatment of Pemetrexed on advanced non-small cell lung cancer patients with fail first-line chemotherapy. The results showed better efficacy and milder side effects of Pemetrexed than Docetaxel, which is the common choice of second-line drug. In addition, treatments of Pemetrexed on several types of malignancies including gastric cancer, breast cancer and pancreatic cancer also revealed the obvious efficacy. Recently, Pemetrexed revealed broader applicability on lung cancer patients and mesothelioma patients.

The other studies indicated that CDA-II, a urinary preparation, also reveals the potency to regulate multiple genes expression. In detail, CDA-II is able to prevent the unlimited proliferation capacity for cancer cells by repairing the abnormality of DNMTs. In addition, treatment of CDA-II also achieves the purpose for cancer therapy by inducing terminal-differentiation and apoptosis. The results from cellular experiment suggested that CDA-II is capable of inducing the apoptosis of promyelocytic leukemia cell lines (HL-60 cells and NB4 cells) and hepatoma cell line (Hep3B). CDA-II is also capable of suppressing the activity of Caspase 3. According to the observation in animal experiments, shrinking of the grafted tumor suggested that treatment of CDA-II on the mice is able to down-regulated the expression of proliferation-related genes including TGF-2, PCNA, c-myc, c-jun, c-fos, N-ras. Moreover, CDA-II arrested the cancer cells in G1 phase (G1 arrest) by up-regulating the expression of cycline-dependent kinase inhibitors such as P16, p21 and P27. In contrast, the expression of cytokines such as cyclin D1 was down-regulated with treatment of CDA-II.

Furthermore, CDA-II is able to suppress the angiogenesis and modulate drug-resistance by inhibiting the expressions of vascular endothelial growth factor (VEGF), basic fibroblast growth factor (bFGF) and drug-resistance factor such as Her-2/neu. In addition, CDA-2 suppresses the metastasis of cancer cells by down-regulating the expression of metastasis related protein such as MMP-9 and Integrin $\beta1$ (IL-$\beta1$). CDA-II also suppresses cancer progression by inhibiting the expression of Peroxisome proliferator-activated receptor $\gamma$ (PPAR)ˆ) to cause the cancer cells death.

Taken together, treatment of CDA-II reveals broader indications with comparison of traditional drugs due to its capacity in affecting multiple targets. It suppresses the growth and metastasis of cancer with milder side effects to achieve the purposes including better efficacy in cancer therapy, prolonged lifespan and improved life quality of patients. Collectively, while the pharmaceutical composition can work in different target or the target worked by the pharmaceutical composition can regulate or affect the progressions of different diseases, it can treat different diseases by administering the pharmaceutical composition to the specific target.

The target therapy drugs are not only applied in cancer therapy, but also utilized for the therapies of other diseases. In another word, the targets of the target therapy drugs are not restricted in cancer-related genes and/or proteins. Practically, the pharmaceutical composition disclosed in Taiwan patent certification no. 1360576 is applied to suppress the expression of sternness genes and drug-resistant genes to improve efficacy of radiotherapy by inhibition of Sirt1 expression. Sirt1 protein triggers lipolysis in mature adipocytes to reduce the stored fat in the body. In skeleton muscle, the Sirt1 activators, such as resveratrol, can activate Sirt1 gene expression to deacetylate and activate PGC-1$\alpha$. Therefore, treatment of the Sirt1 activators activates the genes involving in mitochondrial biogenesis and regulates the genes in the energy metabolism.

Sirt1 gene is located at human chromosome 10. The Sirt1 transcripts distrusting in nucleus and cytoplasm will encode Sirt1 protein with predictive molecular weight about 81.7 kDa. The Sirt1 protein is a member of class III NDA-dependent deacetylase. It controls the epigenetic modification of proteins to promote cellular repair, suppress inflammation, protect neurons, and anti-apoptosis for health improvement and prolonged lifespan.

According to the previous studies, Sirt1 protein inhibits gene expression of UCP2 (Uncoupling protein-2) by binding on its promoter region to regulate insulin secretion and glycolipids metabolism. In cultured hepatocytes, Sirt1 protein maintains cell survival by promoting hepatic glycogenesis through deacetylation of FOXO1. Furthermore, Sirt1 protein also regulates PGC-1α (PPAR-γ Coactivator 1-α), which is a co-activator of PPAR-γ (peroxisomeproliferator-activated receptor γ). In normal physiology, Sirt1 protein activates PGC-1α via direct interaction to elevate expression of hepatic gluconeogenic genes and promote fatty acid oxidation in skeletal muscle. Therefore, Sirt1 is an important target for many target therapy drugs.

Taiwan patent certification no. 1406668 indicated that the mucosal inflammation is suppressed by inhibition of NF-κB (nuclear factor-Kappa B) in *Helicobacter* pylon infected gastric epithelial cells. NF-κB is a nuclear transcriptional factor and consists of two subunits, wherein the subunits of NF-κB include p50, p65, p52, RelB and c-Rel. According to the recent studies, NF-κB plays a critical role in inflammation, apoptosis, necrosis and carcinogenesis. In un-stimulated cells, a family of inhibitors of NF-κB (IκB) in cytoplasm sequesters NF-κB to maintain it in inactive form. With the presence of stimulations, phosphorylation occurred on IκB inactivates its negative function and releases NF-κB. Sequentially, the released NF-κB enters nucleus to activate the down-stream targets by binding on their promoter regions. For example, the inflammation was obviously decreased while NF-κB is stalled in cytoplasm without presence of IKK (IkB kinase) to inhibit IκB activity in IKK knockout rat after spinal cord strauma. In contrast, the presences of xenobiotic agents such as LPS (lipopolysaccharide) or secretory factors released from stimulated cells would inhibit IκB to release and activate NF-κB. The active NF-κB will translocate into nucleus to activate the expression of inflammatory response genes.

Collectively, various genes, growth factors and signal transduction pathways could be utilized as the targets in the development of target therapy drug, such as Sirt1 and NF-κB. However, the previous technologies disclosed in these patents stated above are developed for the therapy of single disease but not designed for multiple applications. In order to improve the defects and reduce the cost of drug discovery, this invention discloses the polypeptide to regulate the physiological conditions in multiple organs, multiple genes and multiple targets manner. For example, Sirt1 protein mediates the deacetylation on p65 and p62, the NF-κB subunits, to prevent the activation of NF-κB that is able to bind on the regulatory regions of the inflammatory response genes. Therefore, Sirt1 protein suppresses inflammation by inhibiting the expressions of inflammatory cytokines such as TNF-α and IL-1β. Development of the pharmaceutical composition targeting to critical mediator is capable of improving and/or curing the relative diseases. The pharmaceutical composition with multiple applications could promote the public interests and save the cost of drug discovery.

SUMMARY OF THE INVENTION

The present invention describes methods for regulating multiple organs, multiple genes and multiple targets by using a polypeptide, wherein the polypeptide comprises the amino acids sequence of SEQ ID No. 1 and its homologies with replacement, deletion, or insertion of one or multiple amino acids.

Another purpose of this invention is providing the method of polypeptide for regulating for regulating multiple organs, multiple genes and multiple targets, comprising administering to a subject a pharmaceutical composition to prevent or treat the subject having at least one disease, wherein the pharmaceutical composition comprising an effective amount of the polypeptide.

In order to achieve the purposes, the embodiments of this present invention disclose a pharmaceutical composition comprising an effective amount of polypeptide, wherein the polypeptide comprises the amino acids sequence of SEQ ID No. 1 or its homologies with replacement, deletion, or insertion of one or multiple amino acids. By administering the pharmaceutical composition to a subject, it can prevent or treat a disease through regulating transcription of multiple genes and expression of multiple targets.

In a representative embodiment, the polypeptide comprises the amino acid sequence of SEQ ID No. 1.

In another embodiment, the polypeptide is the amino acid sequence of SEQ ID No. 1.

In another representative embodiment, the polypeptide comprising amino acid sequence including more than 90% homology with the sequence of SEQ ID No. 1.

In a representative embodiment, the polypeptide is a mediator for regulation of multiple genes expression. For example, the multiple genes include at least one transcriptional factor such as PPAR-γ, NF-κB, Shirt1 or any recombinant of at least genes thereof.

In a representative embodiment, the disease is resulted from abnormal expressions of inflammatory transcriptional factors such as PPAR-γ, NF-κB and Sirt1.

In a representative embodiment, the disease has the symptom of inflammation or associated with inflammation.

In another representative embodiment, the disease is metabolic syndrome disease.

In another representative embodiment, the disease is obesity.

In another representative embodiment, the disease is muscular dystrophy.

In another representative embodiment, the disease is diabetes complications.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE PREFERRED EMBODIMENTS

This invention disclosed the polypeptide comprising the amino acid sequence of SEQ ID No. 1 or its homologies reveal potency for regulating the expressions of multiple genes and multiple targets. In other words, the polypeptide and/or its homologies have the applications including:

(1) the polypeptide affects the expression of multiple genes in multiple organs;

(2) the polypeptide can be provided to the therapy for inflammation and inflammation associated diseases;

(3) the polypeptide can suppress hepatic lipid accumulation;

(4) the polypeptide can inhibit fat accumulation;

(5) the polypeptide can prevent muscular dystrophy; and (6) the polypeptide can reduce the incidence of diabetes complications.

Therefore, it is achievable to improve or treat the multiple genes-associated or multiple targets-associated diseases by administering to a subject a pharmaceutical composition comprising an effective amount of the polypeptide or the homologies thereof, wherein the diseases are resulted from the dysfunctions of lipid metabolism, myogenesis and inflammatory reaction. For example, the disease may be inflammation, muscular dystrophy, obesity, metabolic syndrome and fatty liver.

According to the experiments of this invention, the effective amount of the polypeptide for an adult (60 kg) is at least daily oral administration 0.055 mg/kg-body weight of the polypeptide.

Furthermore, the polypeptide or homologies thereof could be obtained by extraction technology, artificially synthesis or expressed by recombinant organism model.

As used herein, each of the following terms has the meaning associated with it as described below.

The term of homologous polypeptide means the derived polypeptide comprising the amino acid sequence of the polypeptide with replacement, deletion, or insertion of one or multiple amino acids.

The terms "polypeptide" and "protein" are used interchangeably.

Figure 1:
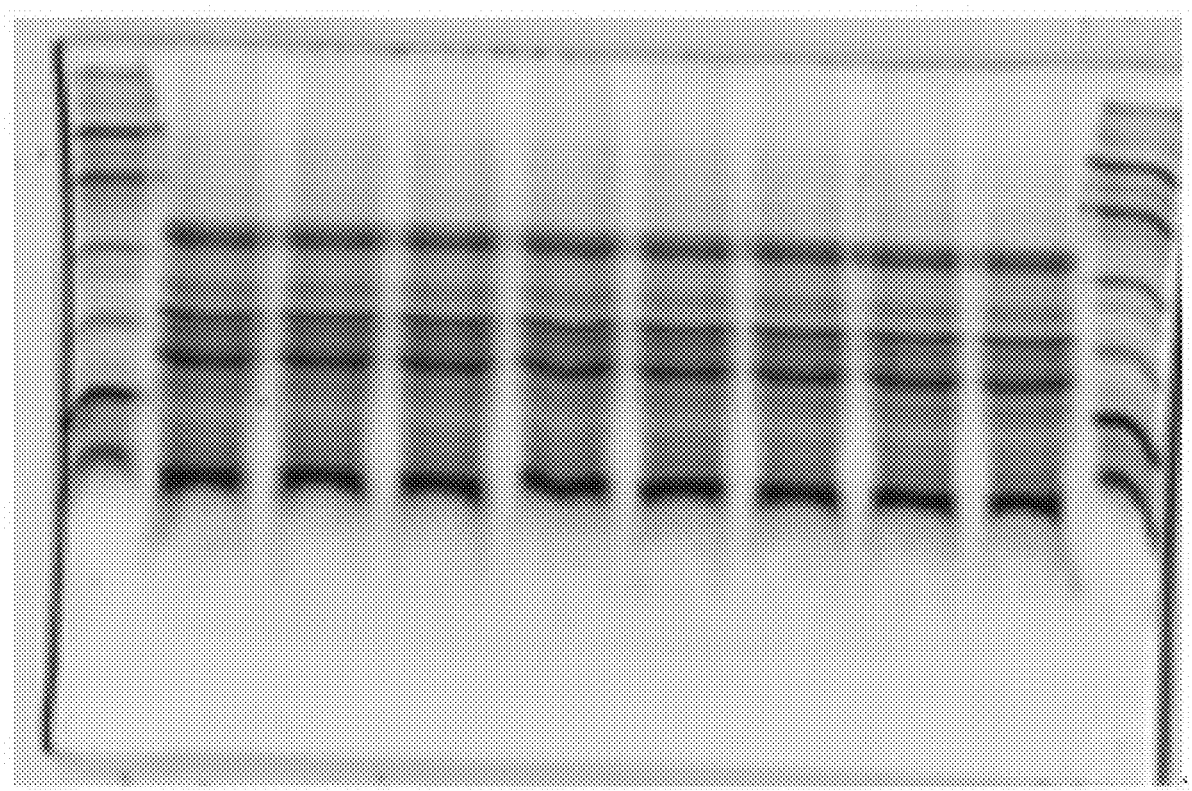
FIG. 1 shows the homologous polypeptides extracted from various Cucurbitaceous plants with capacity for glycemic regulation by SDS-PAGE.

The term of extraction technology means the extracted substance is isolated from the indicated organism such as plant materials upon the difference of solubility in different solvents. Herein, the technologies for isolation and purification in this invention are the known to the person ordinarily skilled in the art. For example, SDS-PAGE is utilized to separate the polypeptide upon the predictive molecular weight. Moreover, liquid chromatography is also used to separate the polypeptides upon different membrane filters. According to the previous studies, several polypeptides obtained from liquid-extraction of Cucurbitaceous plants reveal the function in glycemic control, wherein the polypeptides for glycemic control include the polypeptide of this invention comprising the amino acid sequence of SEQ ID No. 1 and the homologous polypeptides thereof. The Cucurbitaceous plant materials include, but are not limited to, *M. charantia, M. charantia* Linn., *C. moschata, C. lanatus, C. sativus, L. siceraria*, and *T. Radix*. In addition, the result of SDS-PAGE in FIG. 1 reveals that the polypeptides with capacity for glycemia regulation in liquid-extraction of Cucurbitaceous plants are homology. Furthermore, the polypeptide disclosed in this invention comprising the amino acid sequence of SEQ ID No. 1 in this invention or the homologous polypeptides thereof could be also extracted from non-Cucurbitaceous plant materials. For example, the non-Cucurbitaceous plants include *Z. elegans, M. truncatula, C. X paradisi, V. vinifera, S. nigra, O. sativa, A. thaliana* and/or any recombine comprising at least two materials thereof. Collectively, it suggests that the material source to extract the polypeptide comprising the amino acid sequence of SEQ ID No. 1 or the homologous polypeptides thereof is not restricted in Cucurbitaceous plants.

The term of artificial synthesis is known to the person ordinarily skilled in the art. For more, artificial synthesis is to sequentially link amino acids into a polypeptide, wherein the methods of artificial synthesis include chemical peptide synthesis and peptide synthesizer. The artificial synthesis has the following advantages including alteration of primary structure of polypeptide during synthesis processes, addition of specific amino acid and modification on the terminal of polypeptide. Generally, chemical peptide synthesis includes solid phase peptide synthesis and liquid phase peptide synthesis. Herein, purification process of the synthesized peptide intermediates is required when each amino acid is linked into the growing peptide in liquid peptide synthesis. However, the purified peptide intermediates are usually mixture that requires the further purification processes by chromatography. Therefore, the complicated isolation and purification processes are required to obtain the final product with high purity in liquid phase peptide synthesis. The solid phase peptide synthesis is achieved through polymerization of peptide chain that is immobilized on the small porous beads (or the solid particles) in the solvent. In solid phase peptide synthesis, the amino-terminal end is covalently conjugated on the small porous beads and is sequentially linked with the specific amino acids to synthesize the polypeptide. Because the beads are not dissolved in the solvent, the beads could be separated from reagents and side-products by wash and filtration. Therefore, the solid phase peptide synthesis reveals the advantages in better productivity and shorter reaction time cost without the complicated purification to purify the peptide intermediates during the synthesis process compared to the liquid phase peptide synthesis.

The term of recombinant organism model refers to any organism having been genetically modified or genetically engineered. The recombinant organism of the present invention express foreign DNA encoding the polypeptide comprising the amino acid sequence of SEQ ID No. 1 and/or homology thereof, wherein the recombinant organism can be such as *E. coli*, yeast, *lactobacillus* and so on.

The term of foreign DNA refers to genetic material native to one organism that has been placed within a host organism by various means.

The terms of encoding and coding refer to the process by which a gene, through the mechanisms of transcription and translation, produces an amino acid sequence. It is understood that the process of encoding a specific amino acid sequence includes DNA sequences that may involve base changes that do not cause a change in the encoded amino acid, or which involve base changes which may alter one or more amino acids, but do not affect the functional properties of the protein encoded by the DNA sequence. It is therefore understood that the invention encompasses more than the specific exemplary sequences. Modifications to the sequence, such as deletions, insertions, or substitutions in the sequence which produce silent changes that do not substantially affect the functional properties of the resulting protein molecule are also contemplated. The terms of expression and express refer to the transcription and translation to gene product from a gene coding for the sequence of the gene product.

The term of effective dose refers to the weight percentage of the compounds or active constituents in the composition to achieve the prospected effects. According to the well-known knowledge in this field, the effective dose is different due to different deliver manner for different prospected effects. Generally, the weight percentage of active ingredients or compounds in the composition is 1% to 100%, herein, the better effective dose is 30% to 100%.

The term of pharmaceutical composition includes an active pharmaceutical ingredient within at least one pharmaceutically acceptable vehicle. The pharmaceutical composition could be formulated in tablet, powder or injection medicine for different prospective effectiveness. Moreover, the vehicle of the pharmaceutical composition could be solid, semi-solid or liquid. For example, the vectors include, but not restricted by, gelatin, emulsifier, hydrocarbon compounds, water, glycerol, saline solution, PBS, lanoline, paraffin wax, beeswax, dimethyl-silicon oil and ethanol.

The articles "a" and "an" are used herein to refer to one or to more than one (i.e. to at least one) of the grammatical object of the article. By way of example, "an element" means one element or more than one element.

The invention is further illustrated by the following examples. These examples are intended to be representative of the invention and are not to limit the invention, its application, or uses.

In addition, the mice use protocol listed below has been reviewed and approved by the Institutional Animal Car and Use Committee (IACUC) in China Medical University.

Example 1. Preparation of the Polypeptide Comprising the Amino Acid Sequence of SEQ ID No. 1

Figure 2A:
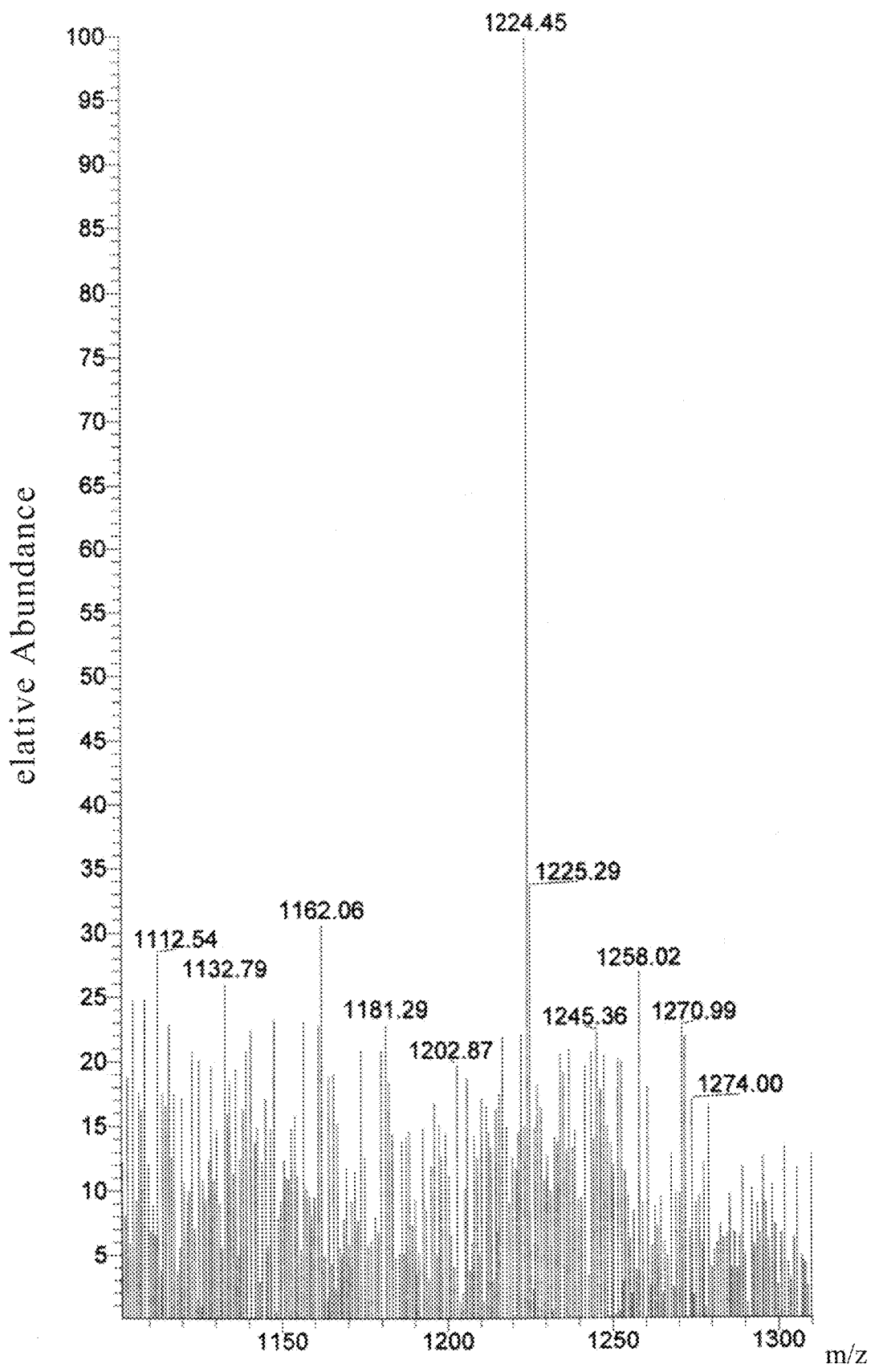
FIG. 2A shows a part of the result of the polypeptide comprising the amino acid sequence of SEQ ID No. 1 in this invention synthesized by automated peptide synthesizer.
Figure 2B:
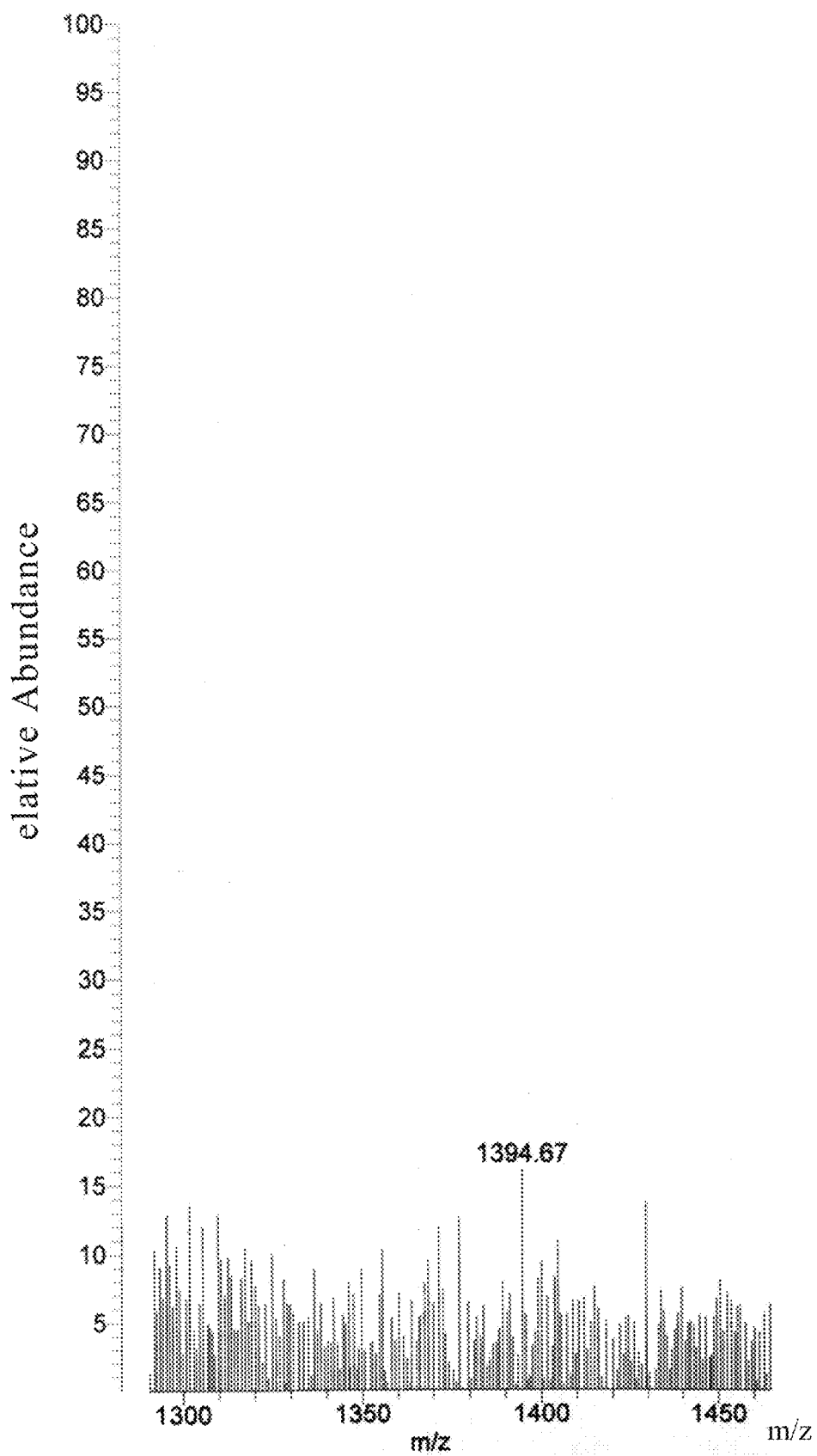
FIG. 2B shows a part of the result of the polypeptide comprising the amino acid sequence of SEQ ID No. 1 in this invention synthesized by automated peptide synthesizer. It is in continue with the FIG. 2A.
Figure 2C:
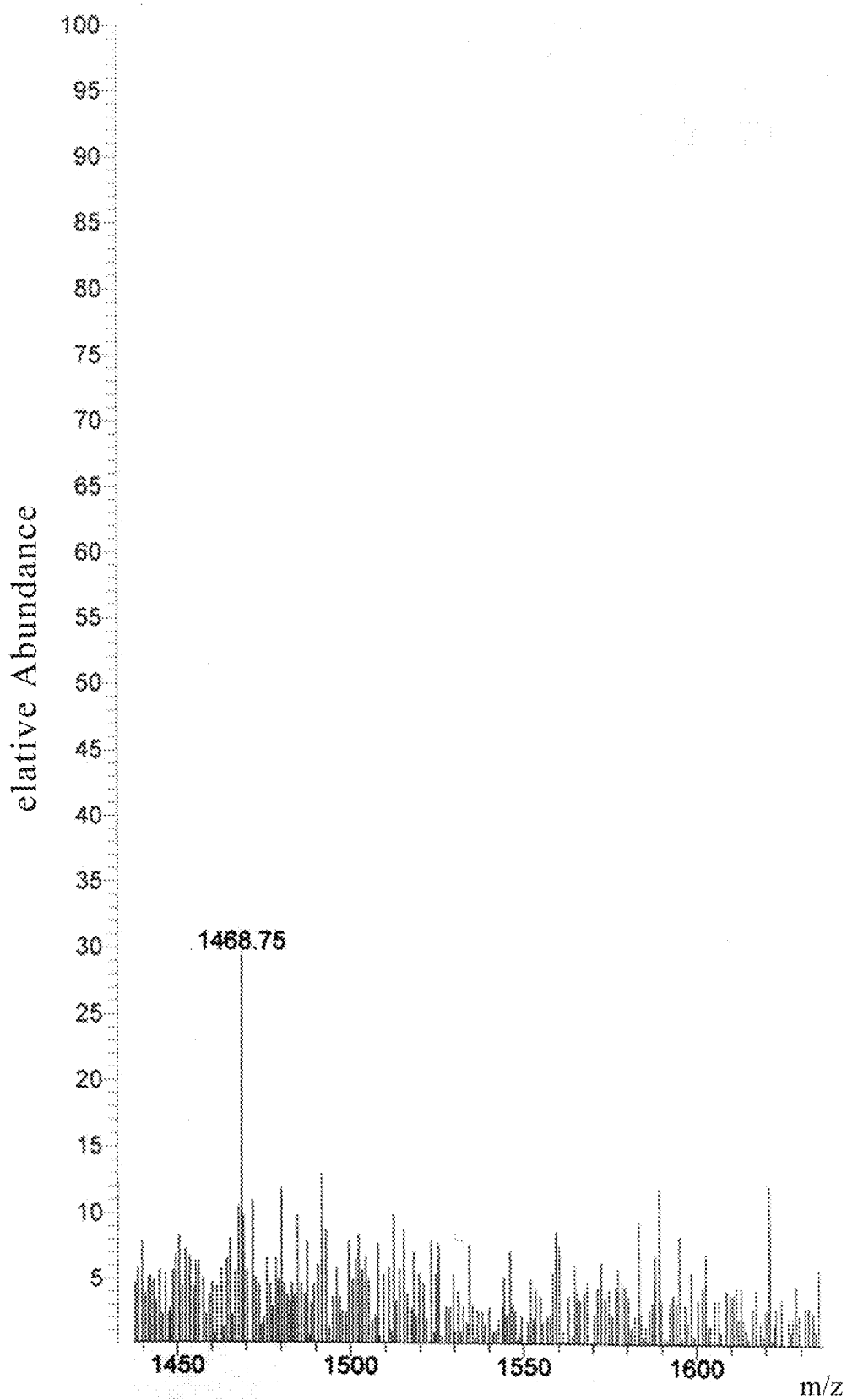
FIG. 2C shows a part of the result of the polypeptide comprising the amino acid sequence of SEQ ID No. 1 in this invention synthesized by automated peptide synthesizer. It is in continue with the FIG. 2B.

The present polypeptide comprising the amino acid sequence of SEQ ID No. 1 is prepared by solid phase peptide synthesis, recombinant organism model or extraction from plant material, wherein the present polypeptide comprising the amino acid sequence of SEQ ID No. 1 shown in FIG. 2 could be synthesized by commercial equipment such as solid phase peptide synthesizer, liquid phase peptide synthesizer and/or microwave phase peptide synthesizer.

Figure 3:
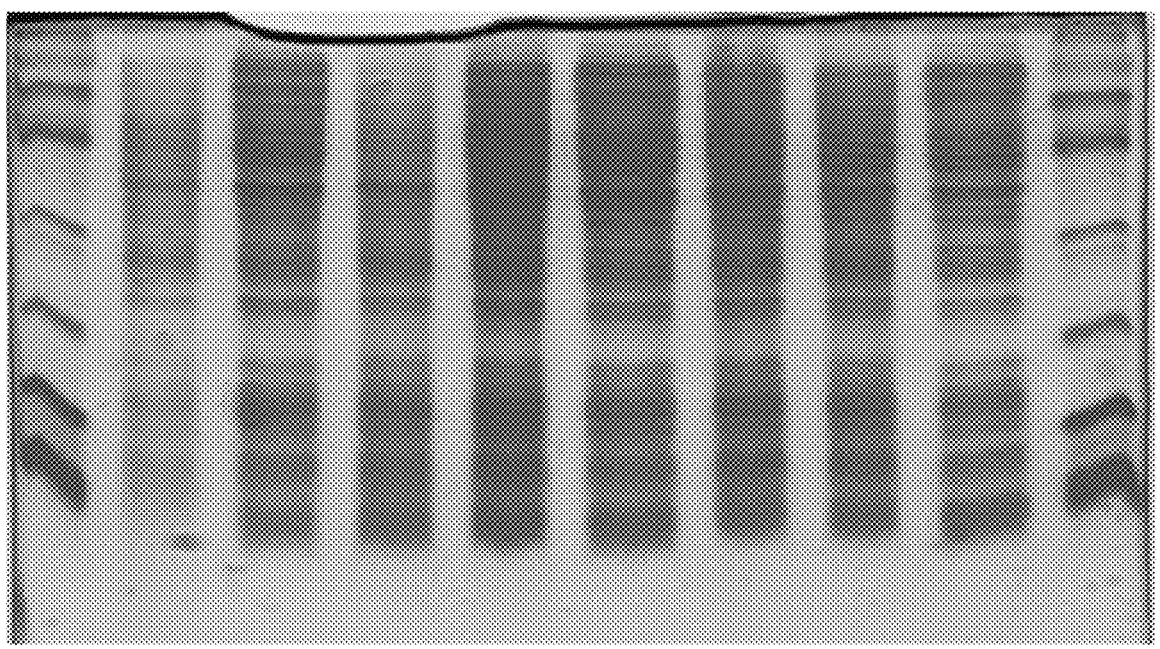
FIG. 3 shows the recombinant polypeptide comprising the amino acid sequence of SEQ ID No. 1 in this invention by SDS-PAGE.

By using bioreactor, plasmid that contains expression cDNA encoding the present polypeptide is transformed into host to express the polypeptide comprising amino acid sequence of SEQ ID No. 1 shown in FIG. 3. Herein, the hosts for expressing the present polypeptide in this invention could be the bacteria including *E. coli* and/or yeast. In addition, the plasmid is selected from the commercial plasmids including pQStrep2, pQStrep4, pGEX-6 µl and/or pQTEV.

The procedure to isolate the present polypeptide from plant material such as *Momordica charantla* is demonstrated as the example for examination. In this example, the present polypeptide in this invention is isolated from extraction liquid of *M. charantla* by using the well-established technologies such as SDS-PAGE and chromatograph. The isolated polypeptide is stored at −80° C. and can be added the preservative such as sodium benzoate or salicylic acid if necessary depending on the situation.

The processes for acquiring the extract liquor include the following steps: First, maceration of *M. charantla* was performed to obtain the crude suspension with solvent such as PBS, citrate buffer solution and/or water. In addition, homogenizer and grinder could be utilized for the maceration. Following, the solid particles were separated from liquid phase by centrifugation with 12,000~15,000 revolution per minute (rpm) and filtration through the membrane with pores about 0.1~0.5 um to obtain a supernatant. Then, the supernatant is sequentially passed through the 10 kDa filter and 1 kDa filter to obtain the filtrate including the extract liquor with the polypeptide of this invention. For example, the filters can be available from Amicon or Millipore.

Example 2. In Vivo Experiments Show the Multiple-Position and Multiple Targets Effects of the Present Polypeptide Materials Mice: The wild-type FVB mice used in the in vivo experiment were purchased from National Laboratory Animal Center. In addition, the mice use protocol listed below has been reviewed and approved by the Institutional Animal Car and Use Committee (IACUC) in China Medical University.

Polypeptide: the polypeptide prepared in example 1 comprises the amino acid sequence of SEQ ID No. 1.

Methods

The wild-type FVB mice were divided into the control group and the experimental group, wherein the mice in the experimental group were daily administered with 20 µl peptide-containing solution that contains 2.5 mmol/kg of the present peptide for 7 days. Moreover, the mice in the control group were daily administrated with 20 µl PBS solution for 7 days.

After the daily administration, the tissues of column, muscle, fat pad, liver and kidney were collected for analyzing the expression of multiple targets by system biology analysis. Herein, the altered expressions of the targets in the genome were determined by using DNA microarray which is a well-established tool for systematic biology analysis. Furthermore, the results of the DNA microarray were further categorized and analyzed by bioinformatics analysis to determine the effect and affected signaling pathways of the present polypeptide. Therefore, it can determine the downstream targets of the present polypeptide comprising the amino acid sequence of SEQ ID No. 1 by the mechanism investigation through microarray analysis and gene expression profile. The detail steps including:

(1) RNA preparation: The total RNA was extracted from the tissue by using RNeasy Mini Kit (Qiagen, Valencia, Calif., USA). The amount of the extracted total RNA was measured by Beckman DU800 spectrophotometer (Beckman Coulter, Fullerton, Calif., USA). In the next step, the quality of the RNA sample with A260/A280 ratio more than 1.8 was further evaluated by Agilent 2100 bioanalyzer (Agilent Technologies, Santa Clara, Calif., USA). When with the RNA integrity number of the sample is more than 8.0, it would be analyzed by the following microarray analysis.

(2) DNA microarray analysis: The procedure of DNA microarray analysis was conducted according to the reference (Cheng, 2007). Briefly, 5 μg of total RNA was amplified by in vitro transcription using MessageAmp™ aRNA kit (Ambion). In the following, the fluorescence dye, Cy5, was chemically labeled on the amplified RNA (aRNA). After the labeling, the fluorescence labeled aRNA was hybridized with Whole Genome OneArray™ in hybridization buffer (Phalanx Biotech Group, Taiwan) on cover slide. Following the hybridization reaction at 50° C. over-night, the non-specific binding on the chip was washed by three washing steps. The washed chip was dried by centrifugation and was scanned by Axon 4000 scanner (Molecular Devices, Sunnyvale, Calif., USA) to measure the fluorescence signals. The fluorescence intensity of Cy5 on each spots was further analyzed by genepix 4.1 (Molecular Devices). First, the signals of each spot were adjusted by deducting the intensity of background. In the next step, the spots including the probes of internal controls or the spots with the signal-to-noise ratios less than 0 would be removed. The qualified spots were normalized by limma package which is belonged to R console (Smyth, 2005).

(3). Analysis of the functional mechanism and affected signaling pathways by using bioinformatics software: The altered downstream targets, functional mechanisms, affected signaling pathways and the disease relevance were investigated by using the bioinformatics software such as Medical Subject Headings (MeSH, http://www.nlm.nih.gov/mesh/meshhome.html) and BiblioSphere Pathway Edition.

The results of bioinformatics analysis were shown in table 1. It results suggested that the present polypeptide comprising the amino acid sequence of SEQ ID No. 1 in this invention actually achieved its functions that affect the signaling pathways and diseases occurrence through a multiple organs and multiple targets manner.

TABLE 1

The altered expression profile of the targets that involve in various signaling pathways in indicated organs.

| Organs | Signal pathway | P value | Genes | Gene description | Fold |
|---|---|---|---|---|---|
| Column | IL-1β signaling pathway | 6.48E–03 | Ccl2 | Chemokine(C-C motif)ligand 2 | Down-regulated 1.71 folds |
| | | | Icam1 | Intercellular adhesion molecule 1 | Down-regulated 2.27 folds |
| | | | Pecam1 | Platelet/endothelial cell adhesion molecule 1 | Down-regulated 1.99 folds |
| | | | Tnfrsf11b | Tumor necrosis factor receptor superfamily 11b (also known as osteoclastogenesis inhibitory factor) | Down-regulated 2.74 folds |
| | | | Cdh2 | Cadherin-2 | Down-regulated 1.73 folds |
| | TNF signaling pathway | 5.21E–06 | Bcl3 | B-cell lymphoma 3 | Down-regulated 1.72 folds |
| | | | Mapk3 | Mitogen-activated protein kinase 3 | Down-regulated 2.32 folds |
| | | | Tnfrsf11b | Tumor necrosis factor receptor superfamily 11B (also known as osteoclastogenesis inhibitory factor) | Down-regulated 2.74 folds |
| | | | ADIPOQ | Adiponectin, C1Q and collagen domain containing | Down-regulated 1.78 folds |
| | | | Casp3 | Caspase-3 | Down-regulated 1.71 folds |
| | | | Ikbke | Inhibitor of kappa kinase epsilon | Down-regulated 1.95 folds |
| | | | Irs1 | Insulin receptor substrate 1 | Down-regulated 1.73 folds |
| | | | Mapk9 | Mitogen activated protein kinase 9 | Down-regulated 1.53 folds |
| | | | Rxra | Retinoid X receptor α | Down-regulated 1.89 folds |
| | | | Ltf | Lactotransferrin | Down-regulated 1.99 folds |
| | | | Socs1 | Suppressor of cytokine signaling 1 | Down-regulated 2.46 folds |
| | | | CD40 | Cell surface antigen, CD40 | Down-regulated 1.79 folds |

TABLE 1-continued

The altered expression profile of the targets that involve in various signaling pathways in indicated organs.

| Organs | Signal pathway | P value | Represented genes | | |
|---|---|---|---|---|---|
| | | | Genes | Gene description | Fold |
| Muscle | IGF signaling pathway | 2.65E−03 | Mdk | Midkine | Up-regulated 3.46 folds |
| | | | Mmp13 | Matrix metallopeptidase 13 | Up-regulated 3.08 folds |
| | | | Spp1 | Secreted phosphoprotein 1 | Up-regulated 3.61 folds |
| | | | Vegfa | Vascular endothelium growth factor alpha | Up-regulated 1.51 folds |
| | | | Cabin1 | Calcineurin-binding protein 1 | Up-regulated 2.49 folds |
| | | | Igfbp5 | Insulin-like growth factor binding protein 5 | Up-regulated 1.99 folds |
| | | | Myh1 | Myosin, heavy polypeptide 1, skeleton muscle, adult | Up-regulated 3.24 folds |
| | | | Irs1 | Insulin-receptor substrate 1 | Up-regulated 3.71 folds |
| | | | Map2k2 | Mitogen-activated protein kinase kinase 2 | Up-regulated 1.65 folds |
| | | | Nfatc3 | Nuclear factor of activated T-cells, cytoplasm andcalcineurin-dependent 3 | Up-regulated 1.56 folds |
| | | | Adprt1 | Poly ADP-ribose polymerase family 1 | Up-regulated 1.94 folds |
| | | | Pik3r1 | Phosphatidylinositol 3-kinase regulated subunit 1 (p85 alpha) | Up-regulated 1.87 folds |
| | | | Rps6kb1 | Ribosomal protein S6 kinase polypeptide 1 | Up-regulated 4.79 folds |
| | | | Twist 1 | Twist homology 1 (*Drosophila*) | Up-regulated 2.16 folds |
| | Adipocytokine signaling pathway | 6.84E−03 | Akt1 | Thymoma viral proto-oncogene 1 | Down-regulated 1.57 folds |
| | | | Cd36 | Cell surface antigen CD36 | Down-regulated 2.42 folds |
| | | | Acsl1 | Acetyl-CoA synthetase long-chain family member 1 | Down-regulated 4.56 folds |
| | | | Nfkbia | Nuclear factor of kappa light chain gene enhancer in B-cells inhibitor, alpha | Down-regulated 2.55 folds |
| | | | Prkag1 | Protein kinase, AMP-activated, gamma 1 non-catalytic subunit | Down-regulated 1.93 folds |
| | | | Ptpn11 | Protein tyrosine phosphatase, non-receptor type 11 | Down-regulated 2.31 folds |
| | | | Stat3 | Signal transducer and activator of transcription 3 | Down-regulated 1.55 folds |
| Fat pad | Fatty acid metabolism | 1.10E−04 | Acox1 | Acyl-coenzyme A oxidase 1 (palmitoyl) | Up-regulated 2.05 folds |
| | | | Cpt1a | Carnitine palmitoyltransferase 1A, liver | Up-regulated 3.1 folds |
| | | | Cpt2 | Carnitine palmitoyltransferase 2 | Up-regulated 1.59 folds |
| | | | Hsd17b4 | Cell surface antigen CD63 | Up-regulated 1.77 folds |
| | | | Acsl4 | Acyl-CoA synthetase long-chain family member 4 | Up-regulated 5.19 folds |
| | | | Sirt1 | Sirtuin 1 (silent mating type information regulation 2, homolog) 1 (*S. cerevisiae*) | Up-regulated 3.09 folds |
| Kidney | Diabetes; Nephrosis | 0.997505 | Apoc3 | Apolipoprotein C-III | Down-regulated 2.5 folds |
| | | | Ctla4 | Cytotoxic T-lymphocyte-associated protein 4 | Down-regulated 1.65 folds |
| | | | Fabp2 | Fatty acid-binding protein 2, intestine | Down-regulated 1.62 folds |
| | | | Fgb | Fibrinogen β chain | Down-regulated 1.91 folds |
| | | | Hp | Heptoglobin | Down-regulated 2.35 folds |

TABLE 1-continued

The altered expression profile of the targets that involve in various signaling pathways in indicated organs.

| Organs | Signal pathway | P value | Represented genes | | |
|---|---|---|---|---|---|
| | | | Genes | Gene description | Fold |
| Liver | Fatty liver | 0.978033 | Mmp2 | Matrix metalloproteinase 2 | Down-regulated 2.11 folds |
| | | | Aldh2 | aldehyde dehydrogenase 2 | Down-regulated 2.5 folds |
| | | | Ctla4 | Cytotoxic T-lymphocyte-associated protein 4 | Down-regulated 1.56 folds |
| | | | Cyp17a1 | Cytochrome P450 family 17, subfamily A, polypeptide 1 | Down-regulated 1.52 folds |
| | | | Mttp | Microsomal triglyceride transfer protein | Down-regulated 3.53 folds |
| | | | Sod2 | Superoxide dismutase 2, mitochondria | Down-regulated 1.71 folds |

Example 3. The Present Polypeptide in the Management of Inflammation and Inflammation-Associated Diseases In example 3, the efficacy of the present polypeptide in the treated mice was determined by whole animal bioluminescent imaging, in vivo bioluminescent imaging in specific organs and immunohistochemistry staining.

Materials

Mice: The NF-κB/luc transgenic mice bearing the luciferase transgene driven by two copies of the NF-kappaB regulatory elements were mated with wild-type FVB mice to generate the hybrid NF-κB/luc transgenic offspring for the experiments.

Polypeptide: The prepared polypeptide comprising the amino acid sequence of SEQ ID No. 1 was utilized in this example.

Methods (1) In Vivo Bioluminescent Imaging

Whole animal bioluminescent imaging: 15 mice with age of 6~8 weeks were randomly divided into three groups. The group 1 was the blank group; the group 2 was control group; and the group 3 was experimental group. The mice of the group 2 and the group 3 were administration with 100 ul of 4 mg/g lipopolysaccharide (LSP) solution to induce the inflammation in the mice by intraperitoneal injection (IP injection). As the blank control, the mice of group 1 were administered with 100 μl of PBS by IP injection. After the LPS-injection for 5 minutes, the mice of the group 3 were further injected with 20 μl solution that contains 0.5 mg/Kg of the present polypeptide by IP injection. In contrast, the mice of the group 2 and the group 3 were injected with 20 μul of water. After 4 hours of the injection, the injected mice were observed for the luciferase activity by whole animal bioluminescent imaging.

Figure 4A:
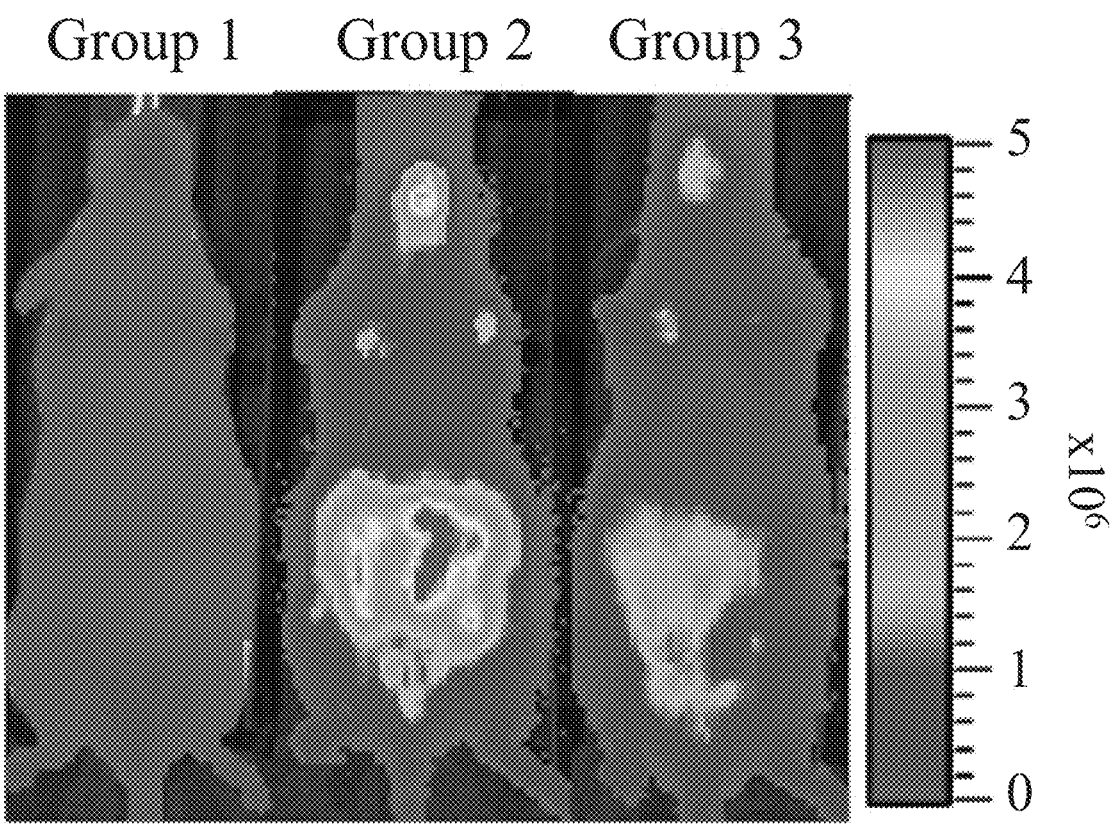
FIG. 4A shows the luciferase activity in the mice of the each group by in vivo imaging system.
Figure 4B:
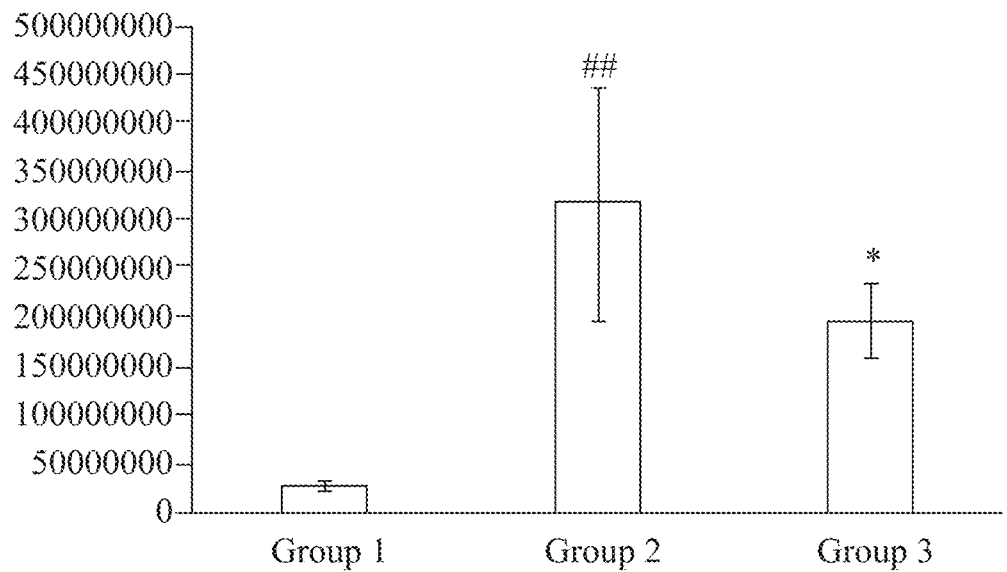
FIG. 4B shows the statistic result of the quantified luciferin value in the mice of the each group.

For in vivo imaging mice were anesthetized with isoflurane and injected intraperitoneally with 150 mg/kg luciferin. After 10 minutes, the mice were placed face up and imaged for 1 min with the camera set at the highest sensitivity by IVIS Imaging System-200 (Series Xenogen Hopkinton, Mass.). The photons emitted from the tissues were quantified by Living Images software (Xenogen, Hopkinton, Mass.) and were shown in FIG. 4A. In the FIG. 4A, the Y-axis shown the signal strength (photons/sec) that stands for total photons diffused from the mice. Moreover, FIG. 4B showed the comparison of the quantified value of luciferin detected from the mice of the each group.

According to the previous studies, NF-κB transcription factor has been shown to activate NF-κB signaling pathway with the presence of LPS in NF-κB/luc hemizygous transgenic mice. In addition, the nuclear NF-κB and the activated NF-κB signaling pathway play the critical role in the immunomodulation. Activation of NF-κB would further activate the expression of inflammation-associated genes. As the results shown in FIGS. 4A and 4B, the average of luciferin value detected from the mice of the group 1 was $2.92 \times 10^7$ photons/sec. In addition, the average of luciferin value detected from the mice of the group 2 was $31.97 \times 10^7$ photons/sec that was stronger than the group 1. Interestingly, the reduced average of luciferin value detected from the mice of the group 3 was $19.82 \times 10^7$ photons/sec. Taken together, the luciferin value detected from the mice of the group 3 was the baseline without LPS-induction. Moreover, the luciferin value diffused from the LPS-injected mice of the group 2. Interestingly, the luciferin value was reduced in the mice of the group 3 with treatments of LPS and present polypeptide.

Therefore, the result from whole animal bioluminescent imaging indicates that LPS was capable of inducing the inflammation in the NF-κB/luc transgenic mice that caused the luminescent signals at the abdomen of the mice. Furthermore, by treating the present polypeptide comprising the amino acid sequence of SEQ ID No. 1, it can obviously decrease the luminescent intensity at the abdomen of NF-κB/luc transgenic mice. As shown in the FIGS. 4A and 4B, LPS induced an approximately 10.95-fold increase of NF-κB-driven luminescent intensity in mice. Moreover, compared to the group 1, the group 3 can has decrease the luminescent intensity, and the suppression was about 38%. Therefore, treatment of the present polypeptide comprising the amino acid sequence of SEQ ID No. 1 can be able to inhibit NF-κB activity for efficient suppression of acute inflammation induced by exogenous stimulations.

(2) Ex Vivo Bioluminescent Imaging

The mice of the three groups manipulated in example 3 were abdominally injected with 150 mg/Kg luciferin. After luciferin injection for 5 minutes, the mice were sacrificed and the tissues including brain, heart, lung, liver, spleen, stomach, kidney, ovary and intestine were rapidly removed. The collected tissues were placed in the IVIS Imaging System-200 Series (Xenogen, Hopkinton, Mass.) and imaged with the same setting used for in vivo bioluminescent imaging. Furthermore, the photons emitted from the tissues were quantified by Living Images software (Xenogen, Hopkinton, Mass.) and shown in FIG. 5, wherein the Y-axis showed the signal strength (photons/sec) that stands for the total detected photons diffused from all indicated tissues in the mice of each group.

Figure 5:
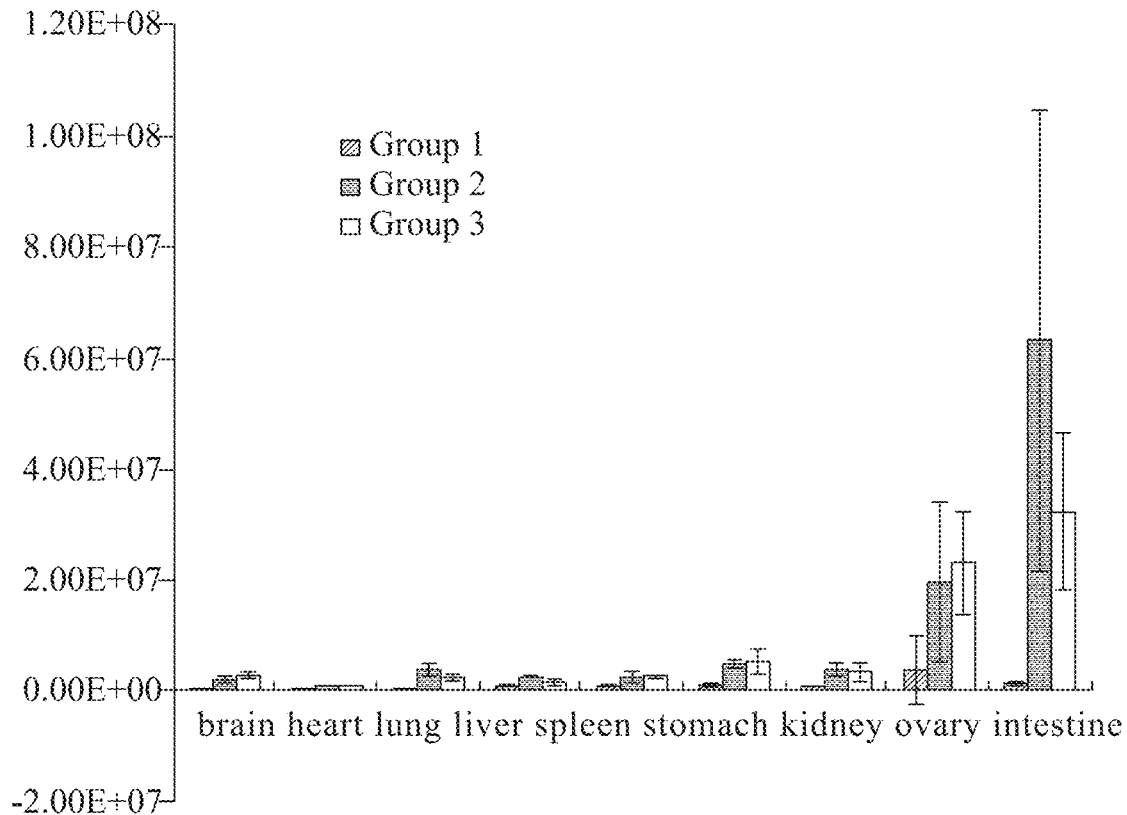
FIG. 5 shows the quantified luciferin value detected from the indicated organs in the mice of the each group.

The results in FIG. 5 showed that the alterations of luciferin emitted from the various tissues in the mice of the each group revealed different trends. With the exception of ovary, the luminescent intensity of the other tissues in the mice of the control group (the group 2) were obviously increased when compared to the blank group (the group 1). With comparison of the control group, the luminescent intensities detected from lung, liver, kidney and intestine in the mice of the experimental group (the group 3) were obviously decreased.

In order to further identify the targeted organs of the present polypeptide in suppression of the inflammation, the quantified luminescent intensities detected from the tissues of the each group were presented as fold change and were shown in the table 2 and table 3 as below. In the table 2, the average of luciferin value in the mice of the group 2 was divided to average of luciferin value in the mice of the group 1 to obtain the fold change. In table 3, the average of luciferin value in the mice of the group 3 was divided to the average of luciferin value in the mice of the group 2 to obtain the fold change.

drated in graded alcohol. Endogenous peroxidase was quenched with 3% hydrogen peroxide in methanol for 15 mins and the nonspecific binding was blocked with 1% bovine serum albumin at room temperature for 1 hour. The blocked sections were further incubated with 50-folds diluted mouse monoclonal antibodies against p56, TNF-α or IL-1β proteins at 4° C. for 16-18 hours, respectively and then incubated with biotinylated secondary antibodies (Zymed Laboratories, South San Francisco, Calif.) that against the Fc fragment of the co-responding first antibody at room temperature for 20 minutes. Finally, the slides were incubated with avidin-biotin complex reagent and stained with 3,3'-diaminobenzidine according to manufacturer's protocol (Histostain®-Plus Kit, Zymed Laboratories, South San Francisco, Calif.).

Figure 6:
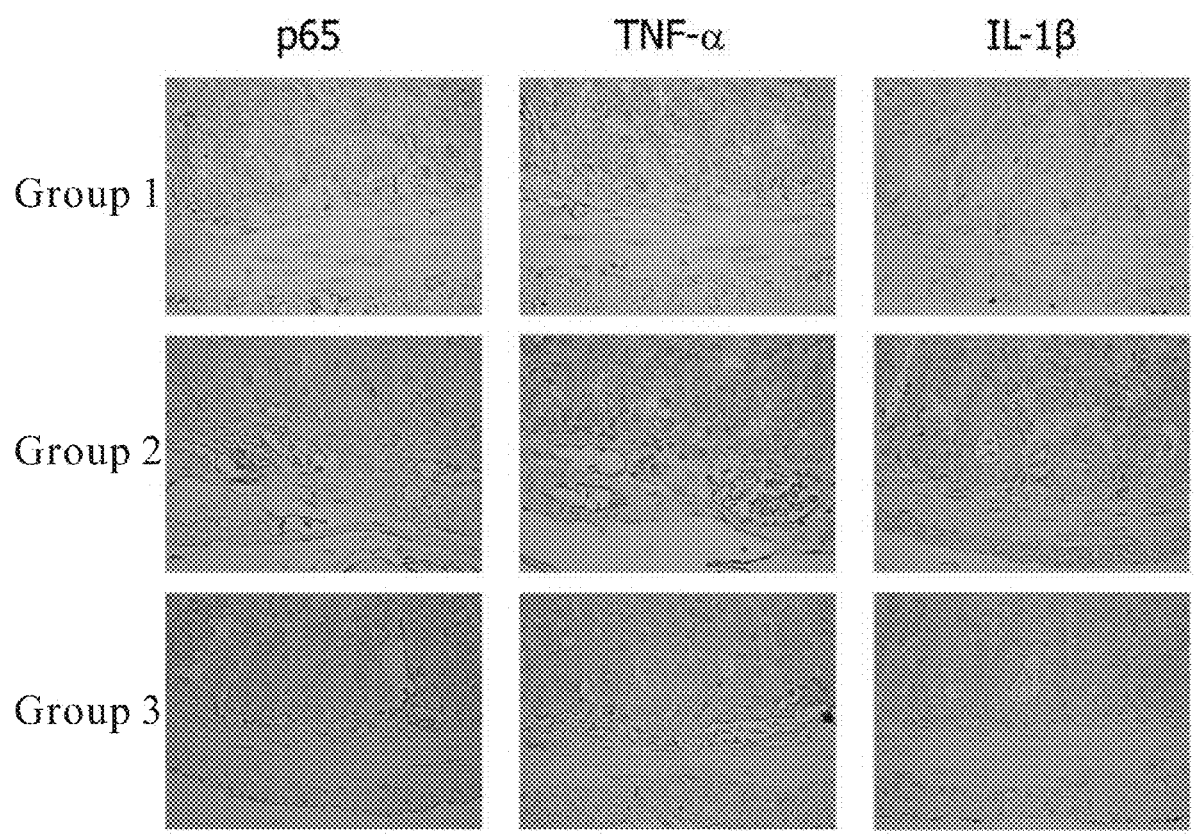
FIG. 6 shows the results of immunohistochemistry staining with antibodies against p65, TNF-a and IL-1b in the mice's organ of the each group.

The expression patterns of p65, TNF-α and IL-1β characterized by IHC were shown in FIG. 6. The results in FIG. 6 showed that the brown signals of TNF-α or IL-1β in the tissue of the control group (the group 2) were obviously increased with comparison of the blank group (the group 1). However, the brown zone that means the active TNF-α and active IL-1β signal pathways in the tissue of the experimental mice (the group 3) were obviously less than the group 2. It disclosed that TNF-α and IL-1β are pro-inflammatory cytokines in acute inflammation and inflammation. Therefore, these results indicated that treatment of the present polypeptide comprising amino acid sequence of

TABLE 2

The fold change of the luciferin value in the indicated organs of group 2 with comparison of group 1.

| Tissue | Brain | Heart | Lung | Liver | Spleen | Stomach | Kidney | Ovary | Intestine |
|---|---|---|---|---|---|---|---|---|---|
| Fold change | 18.87 folds up-regulation | 6.03 folds up-regulation | 11.90 folds up-regulation | 4.06 folds up-regulation | 5.57 folds up-regulation | 4.95 folds up-regulation | 93.78 folds up-regulation | 5.35 folds up-regulation | 55.63 folds up-regulation |

TABLE 3

The fold change of the luciferin value in the indicated organs of each group 3 with comparison of group 2.

| Tissue | Brain | Heart | Lung | Liver | Spleen | Stomach | Kidney | Ovary | Intestine |
|---|---|---|---|---|---|---|---|---|---|
| Fold change | 1.40 up-regulation | 1.13 up-regulation | 1.68 down-regulation | 1.57 down-regulation | 1.08 up-regulation | 1.11 up-regulation | 1.08 down-regulation | 1.17 up-regulation | 1.96 down-regulation |

These results showed that LPS can induce the inflammation and luciferase expression in various indicated organs in NF-κB/luc transgenic mice. However, treatment of the present polypeptide comprising the amino acid sequence of SEQ ID No. 1 can suppress the luciferin value in lung, liver, kidney and intestine. This result indicated that treatment of the present polypeptide can suppress NF-κB activity and the following inflammation reactions induced by LPS in lung, liver, kidney and intestine.

(3) Immunohistochemistry (IHC) Staining Analysis

Immunohistochemistry (IHC) would be known by an ordinary person skilled in the art. The organs were collected from the mice of the each group for paraffin embedding and histology section. The parafilm-embedded organs were cut into 5-lm sections, deparaffinized in xylene and then rehy- SEQ ID No. 1 is capable of suppressing the production of pro-inflammatory cytokine and LPS-induced inflammation.

Example 4. The Present Polypeptide in the Therapy of Fatty Liver

Materials:

Mice: The wild-type FVB mice used in this example were purchased from National Laboratory Animal Center.

Polypeptide: The present polypeptide comprising the amino acid sequence of SEQ ID No. 1 was prepared in example 1.

Methods:

30 wild-type FVB mice were randomly divided into three groups, wherein the mice of the group 1 were the blank group that were fed with normal condition. The mice of the control group (the group 2) and the experimental group (the group 3) were fed with high fat diet. In addition, weekly peritoneal injection with 104l of 10 mmol/kg of the present polypeptide comprising the amino acid sequence of SEQ ID No. 1 was performed on the mice of the group 3 twice for 4 weeks. The mice in the group 2 and the group 3 were peritoneally injected with 100 µl of PBS.

Figure 7A:
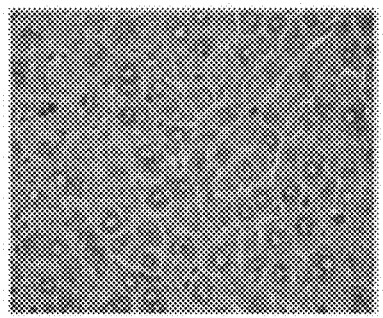
FIG. 7A shows the results of the hepatic tissues in the mice of the each group by H&E staining.
Figure 7A:
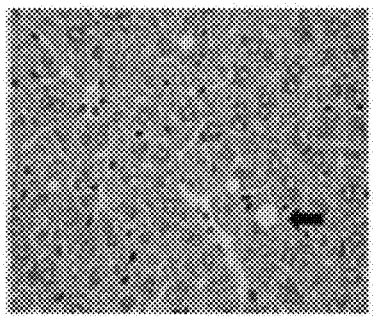
Figure 7A:
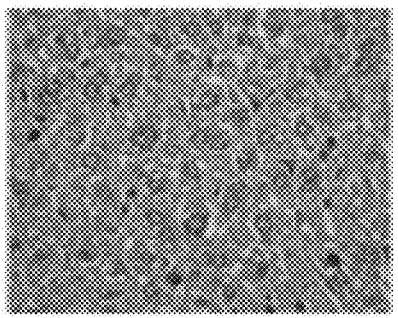
Figure 7B:
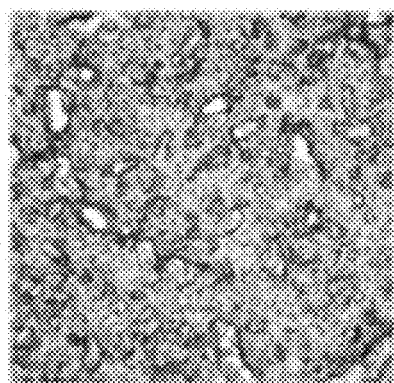
FIG. 7B shows the results of the hepatic fat accumulation in the mice of the each group by Oil-Red staining.
Figure 7B:
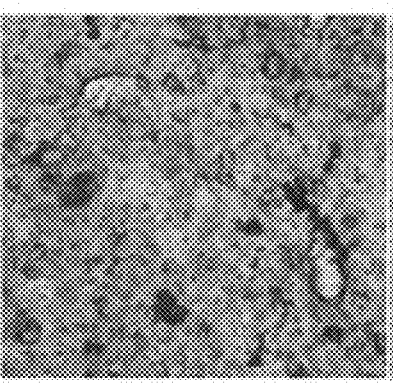
Figure 7B:
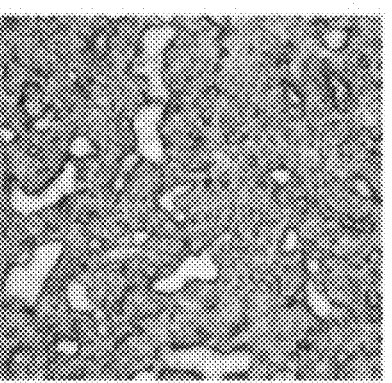
Figure 8A:
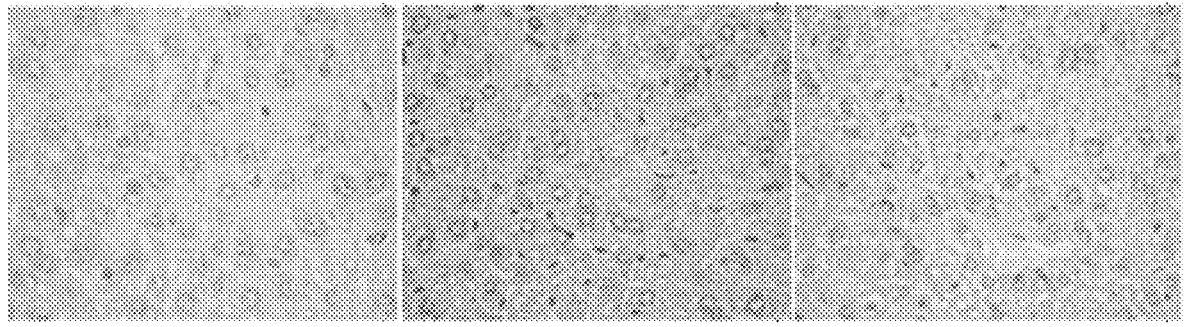
FIG. 8A shows the results of immunohistochemistry staining with antibodies against 4-Hydroxynonenal is performed on the hepatic tissues in the mice of the each group.
Figure 8B:
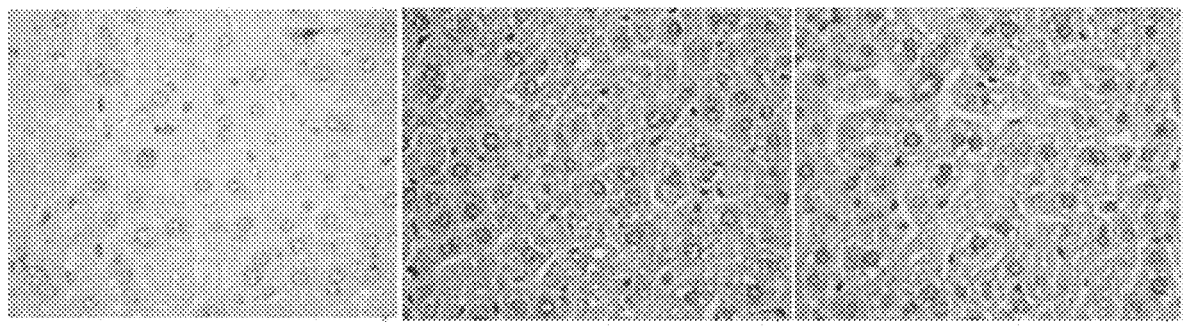
FIG. 8B shows the results of immunohistochemistry staining with antibodies against Malondialdehyde is performed on the hepatic tissues in the mice of the each group.

After the administration, livers in the mice of the each group were collected for the histology sections. The hepatic histology of livers in the mice of the each group was subtracted for H&E staining and oil red-O staining to examined the lipid accumulation in liver, respectively. The hepatic histology of the each group was shown in FIG. 7A and FIG. 7B. Furthermore, the product of lipid oxidation in hepatocytes was examined by IHC staining described in example 3 with antibodies against 4-hydroxynonenal (NHE) or malondialdehyde (MDA) on the hepatic tissues of the each group. The expression patterns of NHE and MDA in hepatocytes of the each group were shown in FIG. 8A and FIG. 8B.

The results in FIG. 7 showed obvious fat vacuoles and massive lipid accumulation in liver of the group 2 with comparison of the group 1. Inspiringly, the mice of the group 3 revealed less lipid accumulation in the liver with comparison of the group 2.

The results in FIG. 8 showed that the control mice of the group 2 acquired more products of lipid oxidation such as HNE and MDA in hepatic tissue with comparison of the group 1. In contrast, the products of lipid oxidation in hepatic tissue were obviously decreased in the mice of the group 3 with comparison of the group 2.

One of an ordinary person skilled in the art knows that the excessive production of lipid oxidation products in the cell would lead to cytopathogenesis and fibrosis. Moreover, HNE and MDA are both products of lipid oxidation that could be the diagnosis biomarker for oxidative damage. Therefore, the present polypeptide comprising the amino acid sequence of SEQ ID No. 1 could efficiently improve the hepatic lipid accumulation and reduce the products of lipid oxidation in hepatocytes. In other words, the present polypeptide comprising the amino acid sequence of SEQ ID No. 1 could be applied for therapy and improvement of fatty liver or hepatic damage-induced disorders.

Example 5. The Present Polypeptide in Suppression of Fat Accumulation

Materials

Mice: In example 5, the genetic deficient mice with massive fat accumulation at abdomen were purchased from National Laboratory Animal Center.

Polypeptide: The present polypeptide comprising the amino acid sequence of SEQ ID No. 1 was prepared in example 1.

Methods

The mice were divided into control group and experimental group. The mice of the experimental group were peritoneally injections with 100 ul of 2.5 nmol/kg present polypeptide comprising the amino acid sequence of SEQ ID No. 1 twice a weeks for 4 weeks. In addition, the mice in the control group were peritoneally injections with 100 ul of PBS.

During the treatment period, the body weight and dietary intake of the mice were recorded at the regular time points. After the treatment, the gross views of whole animals were recorded by photographing. In the following, the fat pads of the mice were collected for the measurement of fat pad weight. The histological examination was performed to determine the number and size of the adipocytes in the mice of the both groups. Furthermore, the percentage of body fat was calculated according the formulation: (fat weight/body weight)×100%, and shown in table 4.

TABLE 4

The body weight, dietary intake, fat weight and body fat of the mice.

|  | Control mice | Experimental mice |
| --- | --- | --- |
| Body weight at start point (g) | 71.99 ± 6.36 | 71.96 ± 6.46 |
| Body weight at end point (g) | 71.95 ± 6.25 | 72.54 ± 7.24 |
| Average dietary intake (g/day/mice) | 0.78 ± 0.22 | 0.88 ± 0.17 |
| Fat weight (g) | 2.53 ± 0.19 | 1.90 ± 0.41 |
| Body fat (%) | 3.68 ± 0.16 | 2.74 ± 0.21 |

Figure 9:
FIG. 9 shows the dorsal views of the experimental mice and the control mice.
Figure 9:
Figure 10:
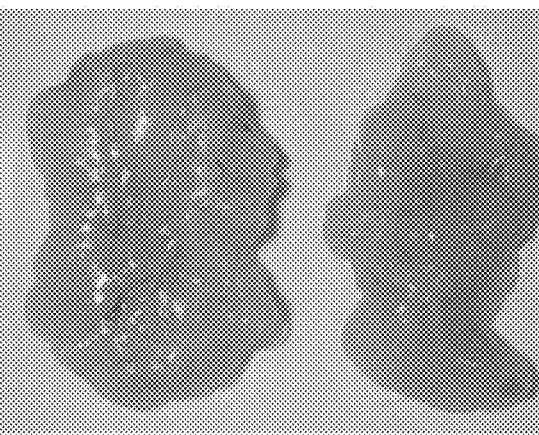
FIG. 10 shows the gross view of the fat pads collected from the experimental mice and the control mice.
Figure 11:
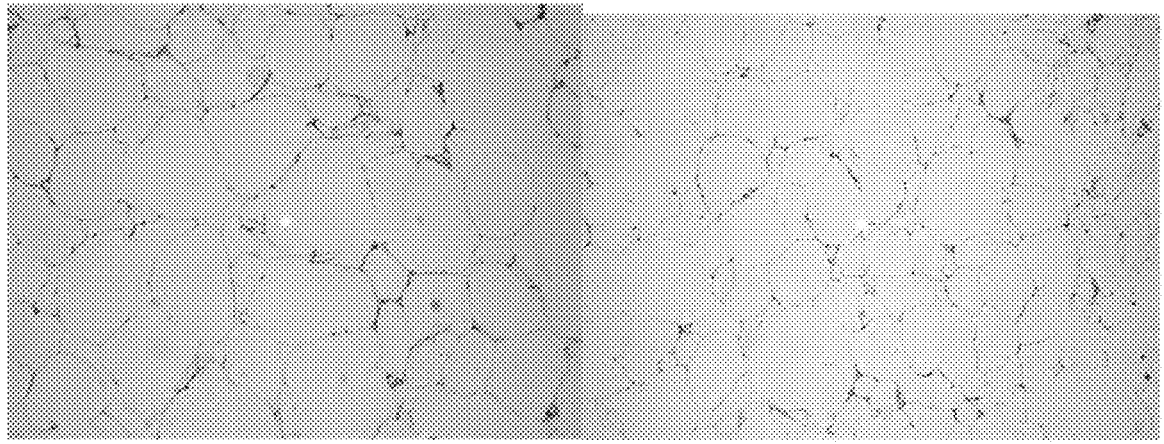
FIG. 11 shows the results of the adipose tissues in the experimental mice and the control mice by H&E staining.

According to the table 4, and FIGS. 9 to 11, it indicated that there was no obvious difference in body weight at start point and in dietary intake during the treatment period between the control group and the experimental group. However, the fat weight and percentage of body fat in the mice of the experimental group were obviously decreased with comparison of the control group. Therefore, the present polypeptide comprising the amino acid sequence of SEQ ID No. 1 in this invention can regulate the adipogenesis to prevent and/or improve the metabolic syndrome.

Example 6. The Present Polypeptide in Prevention of Muscular Dystrophy

Materials

Mice: The genetic deficient mice with massive abdominal fat pad accumulation used in this example are purchased from National Laboratory Animal Center.

Polypeptide: The present polypeptide comprising the amino acid sequence of SEQ ID No. 1 was prepared in example 1.

Methods

Collecting the muscles from the mice of the both groups stated in example 5. The collected muscles were for histological examination. In the histology examination, the cell number and cellular size of the muscular tissue were examined by H&E staining and microscopy observation. The results were shown in FIG. 12.

Figure 12:
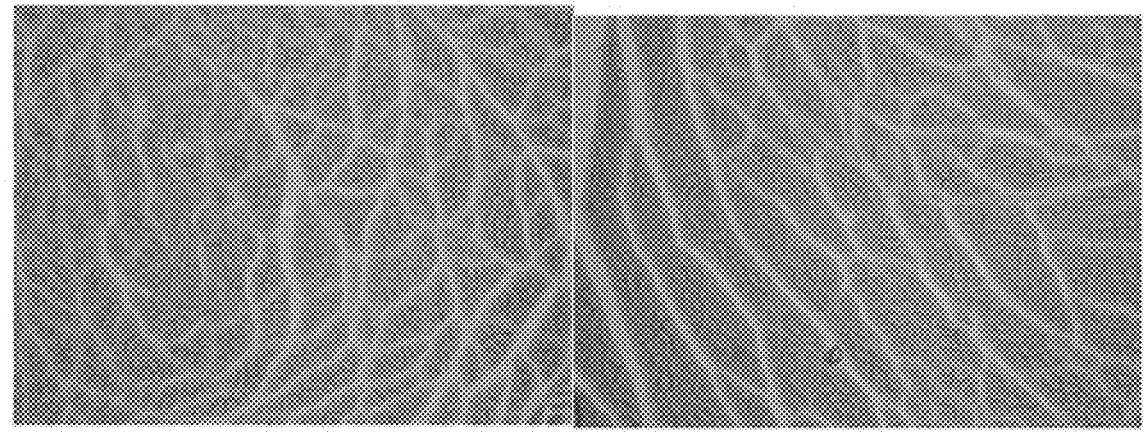
FIG. 12 shows the results of the muscular tissues in the experimental mice and the control mice by H&E staining.

According to FIG. 12, it reveals the pathological characteristics of muscular dystrophy in the control mice. Inspiringly, treatment of the present polypeptide comprising the amino acid sequence of SEQ ID No. 1 actually improved the muscular dystrophy. These results suggested that treatment of the present polypeptide actually affected the myogenesis for prevention and/or therapy of muscular dystrophy.

Example 7. The Present Polypeptide is Capable of Reducing the Incidence and Complications of Diabetes Materials Mice: The Non-obese diabetic mice (NOD mice) used in this example were purchased from National Laboratory Animal Center.

Polypeptide: The present polypeptide comprising the amino acid sequence of SEQ ID No. 1 was prepared in example 1.

Method 23 mice were divided into four groups with different administrations for 20 weeks, wherein 6 mice of the group 1 were control mice that were daily orally administrated with 20 μl of PBS. 6 mice of the group 2 were daily orally administrated with 20 μl of 0.01 umol/kg solution that contained the present polypeptide comprising the amino acid sequence of SEQ ID No. 1. 6 mice of the group 3 were daily orally administered with 20 μl of 0.1 umol/kg solution that contained the present polypeptide comprising the amino acid sequence of SEQ ID No. 1. 5 mice of the group 4 were daily orally administrated with 20 μl of 1 umol/kg solution that contained the present polypeptide comprising the amino acid sequence of SEQ ID No. 1.

During the administration period, the survival rate, incidence of diabetes and diabetes-induced retinopathy in the each group were measured and shown in table 5. After the administration, the blood samples were collected for serological and biochemical analysis. The results were shown in table 6.

TABLE 5

The survival rate, incidence of diabetes and rate of diabetes-induced retinopathy in the mice of the each group

|  | Group 1 | Group 2 | Group 3 | Group 4 |
| --- | --- | --- | --- | --- |
| Survival rate (%) | 4/6 (66.67%) | 6/6 (100%) | 6/6 (100%) | 5/5 (100%) |
| Incidence of diabetes (%) | 2/6 (33.33%) | 0/6 (0%) | 0/6 (0%) | 1/5 (20%) |
| Diabetes-induced retinopathy (%) | 3/6 (50%) | 0/6 (0%) | 1/6 (16.66%) | 1/5 (20%) |

The results in table 5 indicated that the survival rate of the group 1 was 4/6 (66.67%). Moreover, the survival rates of the group 2, the group 3, and the group 4 were 6/6 (100%), 6/6 (100%), and 5/5 (100%), respectively. The incidence of diabetes of the group 1 was 2/6 (33.33%). After administration of the present polypeptide, the incidence of diabetes of the group 2, the group 3 and the group 4 were 0/6 (0%), 0/6 (0%) and 1/5 (20%), respectively. In addition, the rate of diabetes-induced retinopathy of the group 1 was 3/6 (50%). After administration of the present polypeptide, the rate of diabetes-induced retinopathy of the group 2, the group 3 and the group 4 were 0/6 (0%), 1/6 (16.67%) and 1/5 (20%), respectively.

These results suggested that treatment of the present polypeptide in this invention could efficiently elevate the survival rate, reduce the diabetes incidence and/or reduce the related complications such as diabetes-induced retinopathy and nephrosis.

TABLE 6

The serological and biochemical analysis of the each group

|  | Group 1 | Group 2 | Group 3 | Group 4 |
| --- | --- | --- | --- | --- |
| BUN (mg/dL) | 40.50 ± 4.54 | 37.38 ± 2.77 | 38.50 ± 4.69 | 35.88 ± 6.33 |
| Creatinine in serum (mg/dL) | 0.70 ± 0.05 | 0.64 ± 0.12 | 0.69 ± 0.06 | 0.69 ± 0.06 |

The results in table 6 showed that the serum BUN in the mice of the group 1 was 40.50±4.54 mg/dL. With administration of the present polypeptide, the serum BUN concentration in the mice of the groups 2 to 4 were 37.38±2.77 mg/dL, 38.50±4.69 mg/dL, 35.88±6.33 mg/dL, respectively. In addition, the serum Creatinin concentration in the mice of the group 1 was 0.70±0.05 mg/dL. With administration of the present polypeptide, the serum Creatinin concentration in the mice of the group 2, the group 3 and the group 4 were 0.64±0.12 mg/dL, 0.69±0.06 mg/dL, and 0.69±0.06 mg/dL, respectively. The results suggested that administration of the present polypeptide could obviously reduce BUN and Creatinin in the serum. Furthermore, the greater treatment amount of the present polypeptide led to more obvious effect in reducing BUN and Creatinin in the serum.

Collectively, the results in table 5 and table 6 indicated that treatment of present polypeptide comprising the amino acid sequence of SEQ ID No. 1 could actually improve the survival rate, decrease the diabetes incidence, and avoid the diabetes complication and nephrosis. Therefore, treatment of the present polypeptide comprising the amino acid sequence of SEQ ID No. 1 in NOD mice could cure and/or prevent the diabetes and related complications.

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

What is claimed is:

1. A method for treating a disease resulting from abnormal expression of a gene, comprising administering to a subject in need of such treatment an effective amount of a polypeptide to treat the disease of multiple organ failure by regulating transcription of multiple genes selected from the group consisting of Ccl2, Icam1, Pecam1, Tnfrsf11b, Cdh2, Bcl3, Mapk3, ADIPOQ, Casp3, Ikbke, Irs1, Mapk9, Rxra, Ltf, Socs1, CD40, Mdk, Mmp13, Spp1, Vegfa, Cabin1, Igfbp5, Myh1, Map2k2, Nfatc3, Adprt1, Pik3r1, Rps6 kb1, Twist1, Akt1, Cd36, Acsl1 Nfkbia, Prkag1, Ptpn11, Stat3, Acox1, Cpt1a, Cpt2, Hsd17b4, Acsl4, Sirt1, Apoc3, Ctla4, Fabp2, Fgb, Hp, Mmp2, Aldh2, Ctla4, Cyp7a1, Mttp, Sod2, PPAR-γ, and NF-κB;

wherein the polypeptide comprises the amino acid sequence of SEQ ID NO:1;

wherein the disease is selected from the group consisting of muscular dystrophy, inflammation, fatty liver, obesity, diabetes-induced retinopathy, and diabetes-induced nephrosis, and wherein the multiple organs include at least two organs selected from the group consisting of muscle, fatty, lung, liver, kidney, and intestines.

2. The method of claim 1, wherein the multiple organs exclude ovary and heart.

3. The method of claim 1, wherein the polypeptide consists of the amino acid sequence of SEQ ID NO:1.

4. The method of claim 1, wherein the effective amount is from $2\times10^{-7}$ μmol/kg-body weight of the polypeptide to 1 μmol/kg-body weight of the polypeptide by intraperitoneal injection.

5. The method of claim 1, wherein the effective amount to an adult is at least daily oral administration of 0.055 mg/kg-body weight of the polypeptide.

6. The method of claim 1, wherein treating the disease of multiple organ failure comprises regulating expression of multiple targets selected from the group consisting of PPAR-γ, NF-κB and Sirt1.

* * * * *